United States Patent [19]

Harland et al.

[11] Patent Number: 5,670,481

[45] Date of Patent: Sep. 23, 1997

[54] DORSAL TISSUE AFFECTING FACTOR (NOGGIN) AND COMPOSITIONS COMPRISING SAME

[75] Inventors: Richard M. Harland, Berkeley; William C. Smith, Oakland, both of Calif.

[73] Assignee: The Regents of the University of California, Oakland, Calif.

[21] Appl. No.: 297,633

[22] Filed: Aug. 29, 1994

Related U.S. Application Data

[63] Continuation of Ser. No. 939,954, Sep. 3, 1992, abandoned.

[51] Int. Cl.$^6$ .......................... C07K 14/46; C12N 15/09; A61K 38/16
[52] U.S. Cl. .......................... 514/42; 514/13; 514/14; 514/21; 530/399; 530/326; 530/327; 435/69.1
[58] Field of Search .................. 514/12, 13, 14, 514/21; 530/399, 326, 327; 435/69.1

[56] References Cited

U.S. PATENT DOCUMENTS

| | | | |
|---|---|---|---|
| 4,857,637 | 8/1989 | Hammonds et al. | 530/403 |
| 4,933,294 | 6/1990 | Waterfield et al. | 436/501 |
| 5,030,576 | 7/1991 | Dull et al. | 435/69.7 |
| 5,087,616 | 2/1992 | Myers et al. | 514/21 |
| 5,098,833 | 3/1992 | Lasky et al. | 435/69.1 |
| 5,126,134 | 6/1992 | Heim et al. | 424/94.64 |
| 5,149,637 | 9/1992 | Scandella et al. | 435/69.6 |

FOREIGN PATENT DOCUMENTS

| | | |
|---|---|---|
| WO86/06096 | 10/1986 | WIPO . |
| 8606096 | 10/1986 | WIPO . |
| 9102058 | 2/1991 | WIPO . |
| WO 91/03568 | 3/1991 | WIPO . |
| WO 91/03569 | 3/1991 | WIPO . |
| WO 92/05254 | 4/1992 | WIPO . |

OTHER PUBLICATIONS

Bowie et al. 1990. Science 247:1306–1310.
Barinaga. 1993. Science 262: 653–654.
Chen et al., "The Proto–Oncogene C–ros Codes for a Transmembrane Tyrosine Protein Kinase Sharing Sequence and Structural Homology . . .," *Oncogene*, 6 (1991), pp. 257–264.
Christian et al., "Xwnt–8, a Xenopus Wnt–1/int–1–related Gene Responsive to Mesoderm–inducing Growth Factors, May Play A Role in Ventral Mesodermal Patterning During Embryogenesis", *Development*, 111 (1991), pp. 1045–1055.
Sokol et al., "A Mouse Macrophage Factor Induces Head Structures and Organizes a Body Axis in Xenopus," *Science*, 249 (1990), pp. 561–564.
Weiss. 1993. Science 260 : 1072–1073.
Sambrook et al. 1989. Molecular Cloning: A Laboratory Manual. 2nd Ed., pp. 18.79–18.80.
Christian et al. Apr. 1991. Development 111:1045–1055.
Sokol et al. 1990. Science 249: 561–564.
Chen et al. Feb. 1991. Oncogene 6:257–264.
Chalazonitis et al., "Transforming Growth Factor β Has Neurotrophic Actions on Sensory Neurons in Vitro and Is Synergistic with Nerve Growth Factor," *Developmental Biology*, 152, pp. 121–132 (1992).
Smith and Harland, "Expression Cloning of noggin, a New Dorsalizing Factor Localized to the Spemann Organizer in Xenopus Embryos," *Cell*, 70, pp. 829–840 (Sep. 4, 1992).
Smith et al., "Secreted noggin protein mimics the Spemann organizer in Dorsalizing Xenopus mesoderm," *Nature*, 361, pp. 547–549 (11 Feb. 1993).
Christian et al., "Xwnt–8 Modifies the Character of Mesoderm Induced by bFGF in Isolated Xenopus Ectoderm," *The EMBO Journal*, 11:1, pp. 33–41 (1992).
Condie and Harland, "Posterior Expression of a Homeobox Gene in Early Xenopus Embryos," *Development*, 101, pp. 93–105 (1987).
Cooke, "Mesoderm–Inducing Factors and Spemann's Organiser Phenomenon in Amphibian Development," *Development*, 107, pp. 229–241 (1989).
Gallagher et al., "Autonomous Differentiation of Dorsal Axial Structures from an Animal Cap Cleavage Stage Blastomere in Xenopus," *Development*, 112, pp. 1103–1114 (1991).
Kimelman and Maas, "Induction of Dorsal and Ventral Mesoderm by Ectopically Expressed Xenopus Basic Fibroblast Growth Factor," *Development*, 114, pp. 261–269 (1992).
Kao and Elinson, "Dorsalization of Mesoderm Induction by Lithium," *Developmental Biology*, 132, pp. 81–90 (1989).
Slack et al., "Inductive Effects of Fibroblast Growth Factor and Lithium Ion on Xenopus Blastula Ectoderm," *Development*, 103, pp. 581–590 (1988).
Smith and Harland, "Injected Xwnt–8 RNA Acts Early in Xenopus Embryos to Promote Formation of a Vegetal Dorsalizing Center," *Cell*, 67, pp. 753–65 (Nov. 15, 1991).
Sokol et al., "Injected Wnt RNA Induces a Complete Body Axis In Xenopus Embryos," *Cell*, 67, pp. 741–752 (Nov. 15, 1991).

*Primary Examiner*—Vasu Jagannathan
*Assistant Examiner*—Elizabeth C. Kemmerer
*Attorney, Agent, or Firm*—Majestic, Parsons, Siebert & Hsue

[57] ABSTRACT

A novel and soluble polypeptide that is highly conserved among vertebrates has been discovered, which is designated "noggin." The properties of noggin include dorsal growth inducing activity. Noggin and activin act synergistically to produce dorsal mesoderm. Noggin's cDNA has been cloned. Several expression systems have been successfully used to express biologically active noggin. Amino acid sequences representing completely conserved portions as between frog noggin and mouse noggin are:
QMWLWSQTFCPVLY (SEQ ID NO:3);
RFWPRYVKVGSC (SEQ ID NO:4);
SKRSCSVPEGMVCK (SEQ ID NO:5);
LRWRCQRR (SEQ ID NO:6); and,
ISECKCSC (SEQ ID NO:7).

6 Claims, No Drawings

DORSAL TISSUE AFFECTING FACTOR (NOGGIN) AND COMPOSITIONS COMPRISING SAME

This is a continuation of application Ser. No. 07/939,954, filed Sep. 3, 1992, now abandoned.

This invention was made with government support under Grant Contract No. RO1-GM-42341, awarded by the National Institutes of Health. The government has certain rights in this invention.

FIELD OF THE INVENTION

The invention generally relates to growth factors and neurotrophic factors, and more particularly to a soluble growth factor with dorsal growth inducing activity, to complexes including the factor, and to DNA or RNA coding sequences for the factor.

BACKGROUND OF THE INVENTION

Growth factors are substances, such as polypeptide hormones, which affect the growth of defined populations of animal cells in vivo or in vitro, but which are not nutrient substances. Proteins involved in the growth and differentiation of tissues may promote or inhibit growth, and promote or inhibit differentiation, and thus the general term "growth factor" includes cytokines and trophic factors. Among growth, or neurotrophic, factors presently known are those that can be classified into the insulin family [insulin, insulin-like growth factors (e.g., IGF-I, IGF-II), mammary stimulating factor (MSF), and nerve growth factor (NGF)]; those classified into the epidermal growth factor family [epidermal growth factor (EGF) and transforming growth factors (TGFα, TGFβ, TGFγ)]; those classified into the platelet-derived growth factor family [platelet-derived growth factor (PDGF), osteosarcoma-derived growth factor (ODGF), and fibroblast growth factor (FGF)]; the neurotrophins [nerve growth factor (NGF), brain derived neurotrophic factors (BDNF) neurotrophins 3, 4, 5, (NT-3, NT-4, NT-5)]; and others [colony stimulating factor (CSF), T-cell growth factor, tumor angiogenesis factor (TAF), DNA synthesis promoting factor (DSF), tumor-derived growth factors, fibroblast-derived growth factor (FDGF)].

Receptors that affect growth (that is, receptors for growth-associated ligands) are proteins found associated with cell surfaces that specifically bind their growth factors as ligands. Growth factor receptors are utilized in various clinical and diagnostic applications.

U.S. Pat. No. 4,857,637, issued Aug. 15, 1989, inventors Hammonds et al., describes a method for immunizing an animal against its growth hormone receptor through use of vaccinating with antibodies in order to stimulate growth of the animals.

U.S. Pat. No. 4,933,294, issued Jun. 12, 1990, inventors Waterfield et al., describes studies of structural alterations of the human EGF receptor and its gene and a relationship in tumorigenesis for assays and therapies involving the human EGF receptor. For example, such assays can involve detection of structurally altered or abnormally expressed growth factor receptor and the mRNA transcripts and genes which encode them. EGF may have a role in cell proliferation and differentiation since it induces early eyelid opening and incisor development in new born mice.

U.S. Pat. No. 5,030,576, issued Jul. 9, 1991, inventors Dull et al., describes the role of receptors, such as receptors for growth factors, in designing drugs by the pharmaceutical industry, and discloses use of a receptor hybrid for screening drug purposes, such as in studies of EGF binding domains.

U.S. Pat. No. 5,087,616, issued Feb. 11, 1992, inventors Myers and Bichon, describes a method for destroying tumor cells with a composition including a drug conjugate. The conjugate has a growth factor as one moiety and a polymeric carrier with a cytotoxic compound as another moiety. Thus, compositions of the patent are described as binding preferentially to tumor cells bearing EGF-binding receptors (when an EGF growth factor, for example, is used as a first moiety).

U.S. Pat. No. 5,098,833, issued Mar. 24, 1992, inventors Lasky et al., describes a DNA isolant capable of hybridizing to the epidermal growth factor domain. Expression systems for recombinant production are said to be useful in therapeutic or diagnostic compositions.

A good background review of a neurotrophic factor related to NGF is provided by WO92/05254, published Apr. 2, 1992, which also describes state of the art methods of: preparing amino acid sequence variations, site-directed mutagenesis techniques, ligation of coding DNA into a replicable vector for further cloning or for expression, choice of promoters for expression vectors, suitable host cells for expression, particularly mammalian cells, protein purification upon recovery from culture medium as a secreted protein, derivatization with bifunctional agents to cross-link protein to a support matrix for use with antibodies, entrapment in systems for drug delivery, preparation of therapeutic formulations, and methods of administration. In addition, preparation of polyclonal and monoclonal antibodies are described, such as are useful in diagnostic assays. These various aspects of isolation, preparation, and applications for a novel neurotrophic factor, as illustrated by the WO92/05254 publication, are incorporated herein by reference.

Thus, growth factors, their receptors, and DNA or RNA coding sequences therefore and fragments thereof are useful in a number of therapeutic, clinical, research, diagnostic, and drug design applications.

SUMMARY OF THE INVENTION

In one aspect of the present invention a peptide that can be in substantially purified form is characterized by one or more of the following, highly conserved amino acid sequences:

QMWLWSQTFCPVLY (SEQ ID NO:3);
RFWPRYVKVGSC (SEQ ID NO:4);
SKRSCSVPEGMVCK (SEQ ID NO:5);
LRWRCQRR (SEQ ID NO:6); and,
ISECKCSC (SEQ ID NO:7).

Peptides of the invention induce dorsal growth in vertebrates and can be prepared in soluble, physiologically active form for a number of therapeutic, clinical, and diagnostic applications.

In another aspect of the present invention an oligonucleotide, such as cDNA, is provided having substantial similarity to (or being the same as) SEQ ID NO:1 or SEQ ID NO:2. This oligonucleotide can be single or double stranded, be formed of DNA or RNA bases, and can be in the antisense direction with respect to SEQ ID NOS:1 and 2. SEQ ID NO:1 and SEQ ID NO:2 each code for a functional polypeptide that we have designated "noggin," which is capable of inducing dorsal development in vertebrates when expressed.

Noggin or fragments thereof (which also may be synthesized by in vitro methods) may be fused (by recombinant expression or in vitro covalent methods) to an immunogenic polypeptide and this, in turn, may be used to immunize an animal in order to raise antibodies against a noggin epitope. Anti-noggin is recoverable from the serum of immunized animals. Alternatively, monoclonal antibodies may be prepared from cells to the immunized animal in conventional fashion. Antibodies identified by routine screening will bind to noggin but will not substantially cross-react with "wnt" or other growth factors. Immobilized anti-noggin antibodies are useful particularly in the diagnosis (in vitro or in vivo) or purification of noggin.

Substitutional, deletional, or insertional mutants of noggin may be prepared by in vitro or recombinant methods and screened for immuno-cross-reactivity with noggin and for noggin antagonist or agonist activity.

Noggin also may be derivatized in vitro in order to prepare immobilized noggin and labelled noggin, particularly for purposes of diagnosis of noggin or its antibodies, or for affinity purification of noggin antibodies.

DESCRIPTION OF THE PREFERRED EMBODIMENTS

We have discovered a structurally unique growth factor that is readily available in substantially pure, soluble form. We have named the inventive polypeptide "noggin." This newly isolated neurotrophic factor induces dorsal development in vertebrates.

An earlier described family of proteins that also induces dorsal development are the "wnt" proteins. These, however, in contrast to noggin remain tenaciously bound to cell surfaces. Our initial work with noggin has been in Xenopus embryos; however, noggin is highly conserved among vertebrates, as our work with mouse noggin has demonstrated. The prior known FGF growth factor family is also known to be involved in early embryonic induction, but both the FGF proteins and their receptors are distinctly different from noggin. Noggin modifies the actions of FGF (and also activin), for example by potentiating growth, and is thus particularly suggested in therapeutic compositions for use in combination with other growth factors (as therapeutic adjuvants), such as to modify or potentiate their effects.

We have cloned cDNA for noggin. The noggin cDNA contains a single reading frame encoding a 26 kDa protein with a hydrophobic amino-terminal sequence. Noggin is secreted. Noggin's cDNA encodes the protein as a 26 kDa protein, but we have determined that noggin is secreted in vivo, apparently as a dimeric glycoprotein with a starting apparent molecular weight of about 33 kDa (as the wild-type subunit). When not glycosylated, the monomeric unit has an apparent molecular weight on SDS PAGE of about 25–30 kDa.

We have been able to express biologically active noggin in three different systems. Two expression systems we have successfully used to express biologically active noggin have been mammalian cell lines (COS and mouse 293). A third expression system is injection of synthetic mRNA into Xenopus oocytes.

Expression in these several different systems also illustrates the high degree of conservation for noggin. We have found, for example, substantial sequence similarity between frog noggin and mouse noggin with a number of completely conserved stretches. Thus, the following amino acid sequences represent completely conserved portions as between frog noggin and mouse noggin:

QMWLWSQTFCPVLY (SEQ ID NO:3);
RFWPRYVKVGSC (SEQ ID NO:4);
SKRSCSVPEGMVCK (SEQ ID NO:5);
LRWRCQRR (SEQ ID NO:6); and,
ISECKCSC (SEQ ID NO:7).

There is about 87% overall conservation between the mouse and frog sequences, and we have also observed a unique cysteine distribution between the two. We expect human noggin will have substantial similarity to mouse noggin and frog noggin.

Noggin nucleic acids, or oligonucleotides, encode a noggin polypeptide or hybridize to such DNA and remain stably bound to it under stringent conditions and are greater than about 10 bases in length; provided, however, that such hybridizing nucleic acid is novel and unobvious over any prior art nucleic acid including that which encodes or is complementary to nucleic acid encoding other growth factors.

By "stringent conditions" we mean are those which (1) employ low ionic strength and high temperature for washing, for example, 0.15M NaCl/0.015M sodium citrate/ 0.1% NaDodSo$_4$ at 50° C., or (2) use during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

By "substantial similarity," when we are referring to a nucleotide sequence, is meant cross hybridization of sequences under conditions of moderate stringency using a probe greater than 100 nucleotides long at 30° C. in a standard buffer (Wahl et al., PNAS, 76, 3683) and washes at 37° C. in 300 mM NaCl, 30 mM sodium citrate, 0.2% SDS at pH 7. Alternatively, one is able to isolate, by polymerase chain reaction, a fragment of DNA coding for noggin or noggin family members when using primers of degenerate sequence that encode those SEQ ID NOS:3–7.

By "substantial similarity" when reference is made to proteins is that noggin from different species, or noggin family members within a species, will preserve the positions of cysteine residues in at least 80% of positions throughout the protein. Like the neurotrophin family, the sequence of the mature form of noggin and noggin related polypeptides will be identical in at least 40% of positions. Substantial similarity at the protein level includes an ability of a subject protein to compete with noggin for binding to receptors and some (but not all) monoclonal antibodies raised against noggin epitopes.

The cloned cDNA for noggin (derived from frog) is designated herein as SEQ ID NO:1 and from mouse as SEQ ID NO:2. We have used RNA transcripts from the SEQ ID NO:1 clone to rescue embryos and return them to substantially normal development when the noggin RNA is injected into ventralized embryos. In high doses this results in excessive head development and it is for this reason we named the protein "noggin." In northern blot analysis the noggin cDNA hybridizes to two mRNAs that are expressed both maternally and zygotically.

When using nucleotide sequences coding for part or all of noggin in accordance with this invention, the length of the sequence should be at least sufficient in size to be capable of hybridizing with endogenous mRNA for the vertebrate's own noggin. Typically, sufficient sequence size (for example, for use as diagnostic probes) will be about 15 consecutive bases (DNA or RNA). In some diagnostic and therapeutic applications, one may wish to use nucleotide noggin coding sequences (analogous to all or a portion of SEQ ID NO:1 or SEQ ID NO:2) in the anti-sense direction with respect to either SEQ ID NOS:1 or 2.

We suggest as a few preferred primers for amplifying noggin from other species (e.g. human):

| | |
|---|---|
| 5' Primer 1<br>C A A/G A C N T T C/T T G C/T C C N G T N | (SEQ ID:8) |
| 5' Primer 2<br>T T C/T T G G C C N C/A G N T A C/T G T N A A A/G<br>G T N G G | (SEQ ID:9) |
| 5' Primer 3<br>C C N G A A/G G G N A T G G T N T G | (SEQ ID:10) |
| 3' Primer 1<br>C A N C/G T/A A/G C A C/T T T A/G C A C/T T C | (SEQ ID:11) |
| 3' Primer 2<br>C A N A C C A T N C C C/T T C N G G | (SEQ ID:12) |
| 3' Primer 3<br>C G/T N C G/T T/C T G G/A C A N C G/T C C A | (SEQ ID:13) | where N represents a mixture of all four nucleotides nad mixtures of two nucleotides are represented by alternates (e.g. A/G).

Although noggin transcript is not localized in the oocyte and cleavage stage embryo, zygotic transcripts are initially restricted to the presumptive dorsal mesoderm, and reach their highest levels at the gastrula stage in the dorsal lip of the blastopore (Spemann's organizer). In the neurula, noggin is transcribed in the notochord and prechordal mesoderm.

Without being bound by theory, we have formulated hypotheses about the embryological effects of noggin based on where it is expressed, and on the effects of RNA injection in embryos. Since noggin is expressed in the spemann organizer, we believe noggin to be a mediator of the effects of the Spemann organizer, namely neural induction and dorsalization of the mesoderm. Since noggin is expressed in the notochord and head mesoderm, we believe noggin to influence either the dorsal-ventral pattern or anterior-posterior pattern of the neural plate. Since noggin is expressed in the branchial arch neural crest, we believe it may therefore influence whether neural crest cells deposit cartilage and also to influence later branchial arch growth and remodelling. Noggin is expressed in the tail fin neural crest, and since neural crest is required for growth of the fin, noggin may act as a growth factor for epidermis or mesenchyme.

Although much of our experimental work has involved rescue of embryonic development, because expression in the notochord persists in the growing tail bud and a discontinuous line of stained cells (indicating expression of noggin initiated at new sites) runs the length of the roof plate of the neural tube (and is also apparent in the head mesoderm), we believe noggin is expressed as an adult cell function also.

A number of applications for noggin are suggested from its properties.

The noggin cDNA should be useful as a diagnostic tool (such as through use of antibodies in assays for proteins in cell lines or use of oligonucleotides as primers in a PCR test to amplify those with sequence similarities to the oligonucleotide primer, and to see how much noggin is present, e.g. primers such as 5' Primers 1–3 and 3' Primers 1–3).

Because noggin has a pattern of expression that suggests it is used to regulate cartilage production in the embryonic head, clinical uses to regulate cartilage and bone growth are suggested for noggin in therapeutic compositions and particularly in combination with other growth factors due to a property of noggin to potentiate at least some growth factors.

Since neural crest cells are required for the tadpole fin to grow, noggin seems to be a growth factor for the tissue matrix and epidermis and should prove useful, for example, in wound healing compositions.

Noggin, of course, provides the key to isolate its receptor. Since many receptors mutate to cellular oncogenes, the noggin receptor should prove useful as a diagnostic probe for certain tumor types. Thus, when one views noggin as ligand in complexes, then complexes in accordance with the invention include antibody bound to noggin, antibody bound to peptides derived from noggin, noggin bound to its receptor, or peptides derived from noggin bound to its receptor. Mutant forms of noggin, which are either more potent agonists or antagonists, are believed to be clinically useful. Such complexes of noggin and its binding protein partners will find uses in a number of applications.

Practice of this invention includes use of an oligonucleotide construct comprising a sequence coding for noggin and for a promoter sequence operatively linked to noggin in a mammalian or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. The well-known plasmid pBR322 is suitable for most gram negative bacteria, the 2μ plasmid origin for yeast and various viral origins (SV40, polyoma, adenovirus, VSV or BPV) are useful for cloning vectors in mammalian cells.

Expression and cloning vectors should contain a selection gene, also termed a selectable marker. Typically, this is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies.

Examples of suitable selectable markers for mammalian cells are dihydrofolate reductase (DHFR) or thymidine kinase. Such markers enable the identification of cells which were competent to take up the noggin nuclei acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed. Amplification is the process by which genes in greater demand for the production of a protein critical for growth are reiterated in tandem within the chromosomes of successive generations of recombinant cells. Increased quantities of noggin can therefor be synthesized from the amplified DNA.

For example, cells transformed with the DHFR selection gene are first identified by culturing all of the transformants in a culture medium which contains methotrexate (Mtx), a competitive antagonist of DHFR. An appropriate host cell in this case is the Chinese hamster ovary (CHO) cell line deficient in DHFR activity, prepared and propagated as described by Urlaub and Chasin, Proc. Nat. Acac. Sci., 77, 4216 (1980). The transformed cells then are exposed to increased levels of Mtx. This leads to the synthesis of multiple copies of the DHFR gene and, concomitantly, multiple copies of other DNA comprising the expression vectors, such as the DNA encoding noggin. Alternatively, host cells transformed by an expression vector comprising DNA sequences encoding noggin and aminoglycoside 3' phosphotransferase (APH) protein can be selected by cell growth in medium containing an aminoglycosidic antibiotic such as kanamycin or neomycin or G418. Because eukarotic cells do not normally express an endogenous APH activity, genes encoding APH protein, commonly referred to as neo resistant genes, may be used as dominant selectable markers in a wide range of eukaryotic host cells, by which cells transformed by the vector can readily be identified.

Expression vectors, unlike cloning vectors, should contain a promoter which is recognized by the host organism and is operably linked to the noggin nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters can be operably linked to noggin encoding DNA by removing them from their gene of origin by restriction enzyme digestion, followed by insertion 5' to the start codon for noggin.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exit then synthetic oligonucleotide adapters or linkers are used in accord with conventional practice.

Transcription of noggin-encoding DNA in mammalian host cells is controlled by promoters obtained from the genomes of viruses such as polyoma, cytomegalovirus, adenovirus, retroviruses, hepatitis-B virus, and most preferably Simian Virus 40 (SV40), or from heterologous mammalian promoters, e.g. the actin promoter. Of course, promoters from the host cell or related species also are useful herein.

Noggin is believed to find use as an agent for enhancing the survival or inducing the growth of nerve and muscle cells. It, therefore, is useful in the therapy of degenerative disorders of the nervous system ("neurodegenerative diseases"), including such diseases as Alzheimer's disease, Parkinson's disease, Huntington's chorea, ALS, peripheral neuropathies, and other conditions characterized by necrosis or loss of neurons, whether central, peripheral, or motorneurons. In addition, it may be useful for treating damaged nerve cells, e.g., nerves damaged by traumatic conditions such as burns and wounds, diabetes, kidney dysfunction, and the toxic effects of chemotherapeutics used to treat cancer and AIDS. It also is useful as a component of culture media for use in culturing nerve cells in vitro.

Practice of this invention includes preparation and uses of a diagnostic or therapeutic agent comprising a nucleotide sequence of at least about 15 DNA or RNA bases analogous to all or a portion of either SEQ ID NO:1 or SEQ ID NO:2. That is, noggin preparations are useful as standards in assays for noggin and in competitive-type receptor binding assays when labelled with radioiodine, enzymes, fluorophores, spin labels, and the like. Therapeutic formulations of noggin are prepared for storage by mixing noggin having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Inventive complexes comprise a ligand characterized by one or more of the SEQ ID NOS:3–7. The ligand can be bound to a protein, such as antibody. Such antibodies can be polyclonal or monoclonal.

Polyclonal antibodies to noggin generally are raised in animals by multiple subcutaneous (sc) or intraperitoneal (ip) injections of noggin and an adjuvant. It may be useful to conjugate noggin or a fragment containing the target amino acid sequence to a protein which is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$.

Animals can be immunized against the immunogenic conjugates or derivatives by combining 1 mg or 1 µg of conjugate (for rabbits or mice, respectively) with 3 volumes of Freund's complete adjuvant and injecting the solution intradermally in multiple sites. One month later the animals are boosted with ⅕ to ⅒ the original amount of conjugate in Fruend's complete adjuvant by subcutaneous injection at multiple sites. Seven to 14 days later animals are bled and the serum is assayed for anti-noggin titer. Animals are boosted until the titer plateaus. Preferably, the animal is boosted with the conjugate of the same noggin polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

Noggin antibodies are useful in diagnostic assays for noggin or its antibodies. In one embodiment of a receptor binding assay, an antibody composition which binds to all of a selected plurality of members of the noggin family is immobilized on an insoluble matrix, the test sample is contacted with the immobilized antibody composition in order to adsorb all noggin family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

Noggin antibodies also are useful for the affinity purification of noggin from recombinant cell culture or natural sources. Noggin antibodies that do not detectably cross-react with other growth factors can be used to purify noggin free from these other family members.

Aspects of the invention will now be illustrated by the following examples.

EXPERIMENTAL PROCEDURES

Production of Xenopus embryos

Xenopus embryos were prepared by the protocol described by Condie and Harland (*Development*, 101, 93–105, 1987). Embryos were staged according to the table of Nieuwkoop and Faber ("Normal Table of *Xenopus laevis*" (Daubin), Amsterdam: North Holland, 1967). Ventralized embryos were produced by UV irradiation with a Statalinker (Stratagene), and dorsalized embryos were produced by treatment with LiCl as described by us in our paper on certain "wnt" proteins (designated "Xwnt-8"), Smith and Harland, *Cell*, Vol. 67, pp. 753–765 (1991) (incorporated by reference and occasionally referred to hereinafter as "S&H, supra").

EXAMPLE 1

Isolation and Sequencing of Noggin cDNA

The construction of the size-selected plasmid cDNA library from stage 11 LiCl-treated embryos was as follows. Sixty micrograms of poly(A)$^+$ RNA from stage 11 LiCl-treated embryos was size fractionated on a 10% to 30% sucrose gradient in the presence of methylmercuric hydroxide. First strand cDNA was synthesized from 2 µg of the size-fractionated poly(A)$^+$ RNAs primed with oligo(dT) oligonucleotide containing the recognition site for NotI. After synthesis of the second strand, cDNAs were treated with EcoRI methylase, ligated with EcoRI linkers, digested with EcoRI and NotI, and finally ligated to 125 ng of modified pGEM-5Zf(−) (Promega). The pGEM-5Zf(−) used here was modified by the addition of an oligonucleotide into the NsiI site to create an EcoRi site. The vector was not treated with alkaline phosphatase, but the excised polylinker sequence was removed on a sepharose 4BCL column. The ligated products were used to transform XL-I Blue cells (Stratagene), and plated to give 100,000 colonies per 15 cm plate. Plasmid DNAs were isolated form plate cultures by the alkaline-lysis/polyethylene glycol precipitation protocol.

Dorsalizing activity in the library was assayed by injecting RNA transcripts made from pooled plasmid DNA. Single clones were isolated by a process of sib selection. In this procedure the plasmid library was replated on 12 plates with 10-fold fewer colonies per plate. RNA was synthesized from pooled plasmid DNAs isolated from each plate and tested for dorsalizing activity by injection into UV-ventralized embryos. Those pools with dorsalizing activity were replated and screened as described above. This process was repeated until single clones were isolated.

In vitro RNA synthesis, injection assay for dorsal axis rescue and sib-selections were also done, as described by us in S&H, supra.

The nucleotide sequence of both strands of the isolated noggin cDNA clone was determined by the dideoxy termination method using modified T7 DNA polymerase (US Biochem). Deletions were prepared in sequencing templates by both restriction enzyme and exonuclease III digestion (Henikoff, *Meth. Enzymol*, 155, 156–165, 1987).

In vitro translation

One-half µg of in vitro synthesized noggin, Xwnt-8, and goosecoid mRNAs were translated in a nuclease treated rabbit reticulocyte lysate (Promega) with added $^{35}$S-methionine according t the manufacturer's instructions. The translation products were visualized by SDS-polyacrylamide gel electrophoresis (12% gels) followed by fluorography. Noggin protein had the molecular weight predicted by the open reading frame.

RNA Isolation and Analysis

Total RNA was isolated from embryos and oocytes by a small scale protocol as described by Condie and Harland, supra. Dorsal lips were dissected from 30 unfixed stage 10.5 embryos and pooled for total RNA preparation. Samples containing either the total RNA equivalent of 2.5 embryos or approximately 2 µg of poly A+ RNA were analyzed by northern blotting. Random primed DNA probes were prepared from a 1,323 bp fragment of noggin cDNA from the EcoRI site at nucleotide −83 to an EcoRV sites that lies in the vector immediately 3' to the end of the cDNA.

RNAse protection assays were done using a protocol as detailed by Melton et al. (*Nuc. Acids Res.*, 12, 7035–7056, 1984) with minor modifications (C. Kintner, Salk Institute, La Jolla, Calif.). A noggin cDNA exonuclease III deletion clone, illustrated by SEQ ID NO:1 but having a deletion from the 3' end to nucleotide 383, was used as a template for synthesizing RNA probes. The template DNA was linearized by Eco RI restriction enzyme digestion and a 463 base antisense RNA incorporating $^{32}$P was synthesized with T7 RNA polymerase. A 387 base antisense EF1α RNA probe was used as a control for amount of RNA per sample. Probes were gel purified prior to use.

In situ hybridization

After fixation and storage, the embryos were checked to ensure the blastocoel and archenteron were punctured. Care was taken to puncture the residual blastocoel of neurulae and tadpoles as well as the archenteron. Embryos were rewashed at room temperature in 100% ethanol for two hours to remove residual lipid. After hybridization, staining was allowed to develop overnight and the embryos were then fixed in Bouin's. Newly stained embryos have a high background of pink stain but most of this washes out, leaving the specific stain. Following overnight fixation, the embryos were washed well with 70% ethanol, 70% ethanol buffered with PBS and methanol. Embryos were cleared in Murray's mix and photographed with Kodak Ektar 25 film, using a Zeiss axioplan microscope (2.5 or 5× objective with 3×12B telescope to assist with focusing).

Lineage tracing

Lineage tracing with mRNA that encodes nuclear localized β-galactosidase was as we described in S&H, supra. Ventralized embryos were coinjected at the 32 cell stage with 0.5 ng β-galactosidase and 25 pg noggin Δ5' mRNAs. Embryos were fixed and stained with X-gal at approximately stage 22.

Noggin cDNA Encodes a Novel Polypeptide

The 1834 nucleotide sequence of the selected clone is shown by SEQ ID NO:1 and sometimes also referred to as "clone A3." The sequence contains a single long open reading frame encoding a 222 amino acid polypeptide with a predicted molecular weight of 26 kDa. At the amino terminus, the hydrophobic stretch of amino acids suggests that the polypeptide enters the secretory pathway. There is a single potential site for N-linked glycosylation at amino acid 61. Extensive untranslated regions are located both 5' and 3' to the reading frame (593 and 573 bp, respectively). The 3' untranslated region is particularly rich in repeated dA and dT nucleotides, and contains, in addition to a polyadenylation signal sequence located 24 bp upstream from the start of the poly A tail, a second potential polyadenylation sequence 147 bp further upstream.

Sense RNA synthesized from clone A3 with SP6 RNA polymerase was translated in a rabbit reticulocyte lysate system. The $^{35}$S-labeled products were fractionated on a 12% SDS-polyacrylamide gel and visualized by fluorography. The major protein product had the expected molecular weight of approximately 26 kDa.

Comparison of the amino acid sequence of the predicted polypeptide to the National center for Biotechnology Information BLAST network (non-redundant data base) did not identify any similar sequence. Thus, this clone encodes the new type of protein we have named "noggin," which is secreted, and which has dorsal inducing activity in Xenopus.

Noggin mRNA can Rescue a Complete Dorsal-Ventral Axis

Injection of noggin RNA into a single blastomere of a four cell stage UV-ventralized embryo can restore the complete spectrum of dorsal structures. The degree of axis rescue was dependent upon the amount of RNA injected, with embryos receiving low doses having only posterior dorsal structures, while embryos receiving higher doses had excess dorsal-anterior tissue. RNA transcripts from two noggin plasmids were tested. The first contained the full cDNA. The second (pNogginΔ5') had a deletion removing the first 513 nucleotides of the 5' untranslated region up to the Eco RI site. The resulting embryos from injection of RNA transcripts of these two plasmids, as well as Xwnt-8RNA for comparison, were scored according to the dorsoanterior index (DAI) scale of Kao and Elinson (*Dev. Biol.*, 127, 64–77, 1988). In this scale, a completely ventralized embryo is scored as zero, a normal embryo is scored as 5, and the most severely dorsoanteriorized embryos, those having radial dorsoanterior structures, were scored as 10. RNA synthesized from pNogginΔ5' (nogginΔ5' mRNA) repeatedly gave a higher DAI than the equivalent amount of mRNA synthesized from the complete cDNA. The dose-dependency of axis rescue by nogginΔ5' mRNA was very similar to that of Xwnt-8 mRNA.

UV treated embryos were also injected with a higher doses (1,000 pg) of the noggin mRNAs. Injection of this dose of noggin mRNA into one blastomere at the four cell stage resulted in embryos with very severe hyperdorsalization (DAI>7). However, most of these embryos died at the late gastrula/early neurula stage. Apparently excessively strong gastrulation movements resulted in the thinning and rupture of the blastocoel roof. We have also observed this effect with high doses of injected Xwnt-8 mRNA.

The rescue of dorsal development by both nogginΔ5' and Xwnt-8 mRNAs followed a consistent pattern in which increasing amounts of the mRNAs lead to progressively more anterior structures being rescued. For example, embryos that received 1 pg of the RNAs had primarily the posterior and trunk dorsal structures rescued, and for the most part lacked head structures. Higher doses (10 or 100 pg) of both of the RNAs resulted in embryos with more anterior development, and many had either nearly normal or hyperdorsalized phenotypes.

Noggin Injected Blastomeres Act as a Nieuwkoop Center

The effect of varying the site of noggin mRNA injection was investigated. Thirty-two cell stage UV-treated embryos were injected with either 0.5 ng of β-galactosidase mRNA alone or 0.5 ng β-galactosidase mixed with 25 pg nogginΔ5' mRNA. Injection of noggin mRNA into blastomeres of the vegetal tier gave the most strongly dorsoanteriorized embryos. In both of the vegetal injected embryos the nuclear X-Gal staining was found almost exclusively in the endoderm (the mRNA encodes a β-galactosidase that translocates to the nucleus, allowing distinction form the diffuse background stain). One of the embryos shown was strongly hyperdorsalized (DAI approximately 7) as a result of the noggin mRNA injection, and had a severely truncated tail and enlarged head structures. Embryos were also rescued by noggin mRNA injections into the marginal zone. In these embryos β-galactosidase staining was observed primarily in the axial and head mesoderm. Injection of noggin mRNA into the animal pole had very little effect on axis formation. Likewise, β-galactosidase mRNA alone was without effect.

Noggin mRNA is Expressed Both Maternally and Zygotically

In northern blot analysis of RNA from Xenopus embryos two noggin mRNA species of approximate sizes 1.8 and 1.4 kb were observed. A relatively low level of noggin mRNA was detected in oocytes. By stage 11 the level of noggin mRNA was significantly higher, reflecting zygotic transcription (as opposed to the maternally deposited transcripts seen in oocytes). Noggin mRNA remained at the elevated level up to the latest stage examined (stage 45).

We expect that the primary dorsalizing RNA in our library to be elevated in LiCl-treated embryos relative to normal or UV-treated embryos. Lithium ion treatment resulted in a large increase in the amount of noggin mRNA expressed, relative to untreated embryos. UV treatment had the opposite effect. Noggin mRNA expression was essentially undetectable in total RNA samples from these embryos. Thus, the abundance of noggin mRNA in manipulated embryos parallels the rescuing activity.

We analyzed the distribution of noggin mRNA in oocytes and cleavage stage embryos. Since the amount of maternally deposited noggin RNA is too low for in situ hybridization to detect above background, we used an RNAse protection assay. Oocytes were dissected into animal and vegetal halves. No enrichment of noggin mRNA was seen in either hemisphere relative to total oocyte RNA. Four-cell stage embryos were dissected into dorsal and ventral halves, as well as animal and vegetal halves. Noggin transcripts were found to be distributed evenly between dorsal and ventral hemispheres as well as animal and vegetal hemispheres. The same result was obtained with embryos that were tilted 90° immediately following fertilization and then marked with a vital dye on their uppermost side to indicate the future dorsal side. Older (32 cell stage) blastula embryos were also dissected into dorsal-ventral and animal-vegetal halves. No enrichment of noggin mRNA in any of the hemispheres was seen relative to the total embryo. In addition, UV treatment did not alter the abundance of maternally deposited noggin RNA, indicating no preferential degradation in ventral tissues. Samples with known amounts of in vitro synthesized noggin mRNA were included in the RNAse protection assay. From these and other data we estimate that there is approximately 0.1 pg of noggin mRNA per blastula stage embryo and 1 pg per gastrula stage embryo.

The localization of noggin transcripts was investigated in early gastrula stage embryos. Dorsal lips were dissected from stage 10.5 embryos. A northern blot of equal amounts of total RNA from intact embryos, dissected dorsal lips, and from the remaining embryo after dissection of the dorsal lip was hybridized with a noggin probe and then re-hybridized with an EF1α probe, as a control for amount of RNA loaded per sample. The autoradiograph of the blot showed that noggin mRNA at this stage is enriched in the dorsal lip.

In situ Hybridization; Zygotic Expression of Noggin in the Spemann Organizer

The localization of noggin transcripts in developing embryos was examined in greater detail using whole mount in situ hybridization. Whole fixed embryos were hybridized with digoxigenin containing RNA probes. Hybridized RNA probe was then visualized with an alkaline phosphatase-conjugated anti-digoxigenin antibody. The specificity of hybridization seen with antisense noggin probes was tested both by hybridizing embryos with sense noggin probes, and by using two non-overlapping antisense probes. Due both to the low level of expression, and to background staining, noggin mRNA could not be detected unequivocally before the late blastula stage. The increased level of noggin mRNA that was detected by northern blot following activation of zygotic transcription was apparent in in situ hybridization at stage 9 as a patch of staining cells on the dorsal side of the embryo. Viewed from the vegetal pole, this patch of cells was restricted to a sector of about 60°. A side view of the same embryo shows that the staining cells were located within the marginal zone (i.e., between the animal and vegetal poles and within the presumptive dorsal mesoderm forming region). Transcripts are largely restricted to the nucleus at this stage.

A side view of an early gastrula stage embryo (approximate stage 10.5 shows specific hybridization primarily in the involuting mesoderm at the dorsal lip. A vegetal view of the same embryo (blastopore lip arrowed) shows that noggin mRNA is most abundant on the dorsal side, but expression extends at the lower level to the ventral side of the embryo. This method if in situ hybridization does not detect transcripts in the most yolky endodermal region of embryos, therefore we cannot rule out expression in more vegetal regions than those seen in the Figure. Treatments which are known to affect the size of the dorsal lip (LiCl treatment, UV irradiation) had a profound effect on the pattern of noggin in situ hybridization. In LiCl treated embryos the staining is intense throughout the marginal zone. UV treatment reduced the hybridization signal to low levels. This result in consistent with amounts of noggin mRNA seen by northern blot analysis. The UV treated embryo also is a negative control for specificity of hybridization.

As gastrulation proceeds, noggin mRNA staining follows the involuting dorsal mesoderm, and is highest in the presumptive notochord. By the late neurula stage (approximately 18) noggin mRNA expressing cells are clearest in the most dorsal mesoderm, primarily in the notochord but also extending more anteriorly into the prechordal mesoderm. The anterior tip of the notochord is arrowed. During tailbud stages expression of noggin in the dorsal mesoderm declines, through expression in the notochord persists in the growing tailbud. Expression of noggin initiates at several new sites, which become progressively clearer as the tadpole matures. A discontinuous line of stained cells runs the length of the roof plate of the neural tube. Staining is also apparent in the head mesoderm, primarily in the mandibular and gill arches. We suspect that this expression corresponds to skeletogenic neural crest cells. Furthermore, subsets of these cells express homeobox genes that mark different anterior-posterior levels of the head neural crest, for example En-2 in the mandibular arch is seen by antibody staining. Cells with stellate morphology stained from noggin mRNA in the tail fin. These stellate cells are also likely to be derived from the neural crest. None of these patterns were seen with the sense probe, or with a number of other probes.

EXAMPLE 2

Noggin cDNA Transfected into COS Cells Produces Active Conditioned Medium

For COS cells the noggin cDNA was inserted into a COS cell expression vector. COS cells were transfected, and medium harvested after allowing expression of the introduced noggin genes. This medium has been tested in an animal cap assay for mesoderm-inducing or dorsalizing activity. We have tested two transfection protocols, a standard one, where cells recover and then are transferred to serum-free medium, and an alternate where cells are transferred to a defined medium lacking serum but containing transferrin, insulin, and BSA. Cells remain healthy in the supplemented medium and a cotransfected β-galactosidase gene gives 100 fold more activity than in the unsupplemented medium. The results of treating cells with these media is shown below in Table 1. Animal caps were taken from ventralized animals, treated and at the end of neurulation they were scored for elongation, usually a sign that notochord or neural tissues have been induced. Elongation is indicated in Table 1 by a "+" and even greater elongatation a "++." In addition, they are scored for a molecular marker by Northern blotting.

As shown by the data of Table 1, the noggin cDNA has a large effect on the COS cell conditioned medium. However, noggin is probably interacting with something else in the medium, since COS-cell conditioned medium alone has some activity. It is possible that noggin is causing the cells to secrete something that they normally would not, but the experiments do indicate that noggin is secreted and is responsible for some of the activity.

TABLE 1

| COS Cell Conditioned Medium: Effects on Animal Caps | | |
|---|---|---|
| | Elongation | N-CAM expression |
| Transferred to serum free medium + transferrin, BSA, and insulin | | |
| 1. Vector only | +/− | + |
| 2. Noggin cDNA | ++ | ++ |
| Transferred to serum free medium without supplements | | |
| 1. Vector only | − | − |
| 2. Noggin cDNA | − | − |

Noggin mRNA Injected into Oocytes Produces Active Secreted Noggin Protein

A second approach to studying whether the protein can be secreted in active form is to inject oocytes with mRNA and take material secreted by the oocyte. A particular advantage of this method is that the injected mRNA is efficiently translated, and most of the translation of the oocyte can be taken up by the injected mRNA. A new protein, whose synthesis is directed by injected noggin mRNA is secreted into the medium. Noggin clearly synergizes with activin to produce elongated explants that express elevated levels of muscle actin.

Biochemical Properties of Noggin

Injected oocytes are injected with mRNA, and labelled with $^{35}S$ methionine. Most of the radioactive protein secreted into the medium is from the injected mRNA. The noggin protein, which is almost isotopically pure, can then be analyzed. From this analysis we have determined that noggin is a dimeric glycoprotein. When run under reducing conditions, and treated with N-glycanase to remove sugar residues, noggin migrates only slightly slower than its predicted molecular weight of 26 kDa. The removal of sugar side chains results in a loss of about 4 kDa from a starting apparent molecular weight of 33 kDa. When run under non-reducing conditions it migrates at double this value.

We do not yet know if the dimer of 30 kDa protein is the active species, or if there is a proteolytically processed form which is active. In a control experiment with activin mRNA, oocytes produce activin activity, but the bulk of the radiolabelled protein migrates as the precursor form. Only a small amount of processed protein (15 kDa) was detected. It is possible that noggin injected oocytes secrete predominantly unprocessed protein and a trace of extremely active processed protein that we have not detected. Despite the caveats, the main point from analysis of injected oocytes and transfected COS cells is that active noggin can be obtained as a freely soluble secreted polypeptide. This sets it apart from the other group of genes with dorsalizing activity, the wnts. Wnt proteins have not been available in soluble form and this has greatly hampered the analysis of their biological activities, and of the receptor that binds to them.

EXAMPLE 3

Cloning of the Mouse Noggin Homolog

It is currently impossible to eliminate zygotic noggin transcription from developing Xenopus embryos. In contrast, it should be possible to generate homozygous null mutations in the mouse. We have cloned the mouse noggin cDNA (SEQ ID NO:2). This is useful to generate mutant mice. In addition to generating the probes and tools to make mutant mice, a comparison of the noggin sequences should be a useful predictor of conserved domains and functions. The C-terminal 80 amino acids are 87% identical between SEQ ID NOS:1 and 2.

Mouse noggin was isolated from an embryonic cDNA library by probing with a radiolabelled frog noggin cDNA under conditions of moderate stringency (as defined earlier). Subsequently a genomic clone was isolated by probing a genomic library with the mouse noggin cDNA under conditions of high stringency (as defined, but hybridized at 42° C. and washed at 50° C. in 15 mM NaCl, 1.5 mM sodium citrate).

It is to be understood that while the invention has been described above in conjunction with preferred specific embodiments, the description and examples are intended to illustrate and not limit the scope of the invention, which is defined by the scope of the appended claims.

---

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 1834 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Xenopus laevis
        ( D ) DEVELOPMENTAL STAGE: Gastrula ( x ) PUBLICATION INFORMATION:
        ( A ) AUTHORS: Smith, William C.
                Harland, Richard M.
        ( B ) TITLE: Expression Cloning of noggin, a New
                Dorsalizing Factor Localized to the Spemann
                Organizer in Xenopus Embryos
        ( C ) JOURNAL: Cell
        ( D ) VOLUME: 70
        ( F ) PAGES: 829-840
        ( G ) DATE: Sept. 4-1992

( x i ) SEQUENCE DESCRIPTION: SEQ ID NO:1:

```
CTAATAAATC  CTAAGTAGCC  AGAGGGACGA  GCTACAGACT  GGTTGCGGCG  CAGGGTTTAT    60

CCAGGGCAGA  GAGGAGCAGC  AAAAGCACAT  TGCGCAGCTC  TCACTCCCCC  TTTCCTTCTG   120

CTTCACTCTA  TAAGGGCTCC  TGCAAATGAA  AGAGACCTGC  GGGGATTTGC  GCGGACAGAT   180

GTAAAGGAGA  TCCTGCAACT  TTCTCTGGTT  GCATCCCTGG  GAGTCGCTGC  GCGCCGCTGG   240

CTGATTGCGA  CTGTTGCTTT  CCACAGCTCC  CTTCTTCCGC  AGTTTCTTCT  AGGAGCAGAT   300
```

```
CGAGTCTCTG GTTACCATGG TGATCGAGCT GAAAGTGAAG AATATTTAAG AGAGGGGAGG      360
CTGGAGCCAG CAGGCAGACA AAGTGGTGCC ACCAAGGACT GTGCGTAAAG GGTGAGCGCA      420
TTGGAGACAG ACAGGGGCTC TGCTGAACTT CCACTTGACT GCGATGAGAG GGGGGAATCC      480
CCAATTCGCT AGGTGCCCCT GAACCCCCCA GAATTCCTCC TCTGATGCAT TATTTATGAT      540
CTCTGGCAAG AAATCGGGAG CACCCAACTC TTATTTTGTG CAGCTGTGTG CAGCATGGAT      600
CATTCCCAGT GCCTTGTGAC TATATATGCT CTGATGGTCT TCTTGGGACT TAGAATAGAC      660
CAAGGGGTT GCCAACATTA TCTGCACATC AGACCGGCTC CTAGTGAAAA CCTACCACTG       720
GTGGACCTTA TTGAGCACCC GGATCCCATC TATGATCCCA AGGAGAAGGA TCTTAACGAG      780
ACCTTGCTGA GGACTTTAAT GGTTGGACAC TTTGACCCCA ACTTTATGGC CACCATCCTG      840
CCAGAGGAGA GACTTGGAGT GGAGGACCTT GGGGAGTTGG ATCTCCTTCT TAGGCAGAAG      900
CCCTCGGGGG CAATGCCAGC GGAAATCAAG GGACTGGAGT TTTACGAGGG GCTTCAGAGC      960
AAAAAGCACA GACTGAGCAA GAAACTCAGG AGAAAGTTGC AGATGTGGCT CTGGTCCCAG     1020
ACCTTCTGTC CTGTCCTTTA CACATGGAAT GACCTAGGGA CCAGGTTTTG GCCTCGCTAT     1080
GTGAAAGTAG GGAGCTGCTA CAGTAAGAGG TCTTGTTCTG TGCCAGAGGG CATGGTTTGC     1140
AAAGCTGCCA AGTCTATGCA TTTGACCATC TTAAGGTGGA GATGTCAACG CAGGGTTCAG     1200
CAGAAGTGTG CGTGGATAAC CATTCAGTAC CCTGTCATTT CCGAGTGCAA ATGCTCATGC     1260
TGAGACTCTT GGACTAATGC AAAAAGACAG TAGCTTCATG GTTCAAGCTT CATGTTATAT     1320
GCACTGTAAT ATGTAGAAAT GTATATGTGT GTATATATGG CATTGGTCTA AATTACTATT     1380
AAAAGGTCAG TATTATTCTT TTAAATAACC AGTGTCTACT GTATTCCAA CACTATATC       1440
CTGGTTGTGT TTTATTTTAA TAATATTATT ATTATTTTT TTTTGCCTAA TGTATCTCTA      1500
TTTATATCCA AAAAAAGAGC ACTTCGCTTG GCGAAGCATT TTTTTTAAA GAAAAAAAA       1560
ACAAATTTAA TAGTTTAATA ATATAGAAGC ATTTTTTCC TTTAATGGAA AATGTGCCTT      1620
TTTTTGATGG ACCTCAAAAA AAAAATGAAT AAAAACCAGA GCAAGATATA ATTTCAGTT      1680
TATTGTACAT AGAAAGAGAA CACATTTTGA AAGATGAAAA ATTTACTCT TGTAAATGAG      1740
AACTATCTGC TATTTATTCT TTTATTTTTT TTTTCCTCCC CCTGTAGAGT GCAGAATAAA     1800
AGTAAACCAC TAAAATATTA AAAAAAAAA AAAA                                  1834
```

( 2 ) INFORMATION FOR SEQ ID NO:2:

( i ) SEQUENCE CHARACTERISTICS:
        ( A ) LENGTH: 356 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mus musculus
        ( D ) DEVELOPMENTAL STAGE: Gastrula ( x i ) SEQUENCE DESCRIPTION: SEQ ID NO:2:

```
GCAGATGTGG CTGTGGTCAC AGACCTTCTG CCCGGTGCTG TACGCGTGGA ATGACCTAGG       60
CAGCCGCTTT TGGCCACGCT ACGTGAAGGT GGGCAGCTGC TTCAGCAAGC GCTCCTGCTC      120
TGTGCCCGAG GGCATGGTGT GTAAGCCATC CAAGTCTGTC CACCTCACGG TGCTGCGGTG      180
GCGCTGTCAG CGGCGCGGGG GTCAGCGCTG CGGCTGGATT CCCATCCAGT ACCCCATCAT      240
```

```
TTCCGAGTGT  AAGTGTTCCT  GCTAGAACTC  GGGGGGGCCC  CCTGCCCGCG  CCCAGACACT         300

TGATGGATCC  CCACCAACGN  CCCCCTACC   CCCACCACCT  CCAACCAGTT  TCACCA            356
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

```
Gln  Met  Trp  Leu  Trp  Ser  Gln  Thr  Phe  Cys  Pro  Val  Leu  Tyr
 1                    5                        10
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

```
Arg  Phe  Trp  Pro  Arg  Tyr  Val  Lys  Val  Gly  Ser  Cys
 1                    5                        10
```

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

```
Ser  Lys  Arg  Ser  Cys  Ser  Val  Pro  Glu  Gly  Met  Val  Cys  Lys
 1                    5                        10
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

Leu Arg Trp Arg Cys Gln Arg Arg
1               5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

Ile Ser Glu Cys Lys Cys Ser Cys
1               5

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHESIZED DNA"

( i i i ) HYPOTHETICAL: NO ( i v ) ANTI-SENSE: NO ( x i ) SEQUENCE DESCRIPTION: SEQ ID NO:8:

CARACNTT YT  G Y CCNGTN                                                                18

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHESIZED DNA"

( i i i ) HYPOTHETICAL: NO ( i v ) ANTI-SENSE: NO ( x i ) SEQUENCE DESCRIPTION: SEQ ID NO:9:

TT Y TGGCCNM GNTA Y GTNAA RGTNGG                                                        26

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHESIZED DNA"

( i i i ) HYPOTHETICAL: NO ( i v ) ANTI-SENSE: NO ( x i ) SEQUENCE DESCRIPTION: SEQ ID NO:10:

CCNGARGGNA TGGTNTG 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHESIZED DNA"

( i i i ) HYPOTHETICAL: NO ( i v ) ANTI-SENSE: NO ( x i ) SEQUENCE DESCRIPTION: SEQ ID NO:11:

CANSWRCA Y T TRCA Y TC 17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHESIZED DNA"

( i i i ) HYPOTHETICAL: NO ( i v ) ANTI-SENSE: NO ( x i ) SEQUENCE DESCRIPTION: SEQ ID NO:12:

CANACCATNC C Y TCNGG 17

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHESIZED DNA"

( i i i ) HYPOTHETICAL: NO ( i v ) ANTI-SENSE: NO ( x i ) SEQUENCE DESCRIPTION: SEQ ID NO:13:

CKNCK Y TGRC ANCKCCA 17

It is claimed:

1. A substantially pure polypeptide characterized by a physiologically active, soluble form and comprising an amino acid sequence identical to that encoded by the DNA of SEQ ID NO:1, said polypeptide having neurotrophic activity.

2. The polypeptide as in claim 1 being isolated from a recombinant expression system or from an animal species substantially free of contaminating polypeptides of said animal species.

3. The polypeptide as in claim 1 wherein the neurotrophic activity is determinable in vitro as dorsal development induction in embryonic frogs.

4. A composition comprising the polypeptide of claim 1 and a physiologically acceptable carrier with which the polypeptide is admixed.

5. The composition as in claim 4 wherein the carrier is a solvent in which the peptide is dissolved.

6. The composition as in claim 4 wherein the neurotrophic activity includes dorsal or neural development induction in embryonic vertebrates.

* * * * *